(12) United States Patent
Becker et al.

(10) Patent No.: US 7,772,323 B2
(45) Date of Patent: Aug. 10, 2010

(54) CONJUGATED COPOLYMERS, REPRESENTATION AND USE THEREOF

(75) Inventors: Heinrich Becker, Hofheim (DE); Esther Breuning, Niedernhausen (DE); Aurélie Falcou, Frankfurt (DE); Amir Parham, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 982 days.

(21) Appl. No.: 10/567,934

(22) PCT Filed: Aug. 12, 2004

(86) PCT No.: PCT/EP2004/009018
§ 371 (c)(1),
(2), (4) Date: Feb. 9, 2006

(87) PCT Pub. No.: WO2005/014688
PCT Pub. Date: Feb. 17, 2005

(65) Prior Publication Data
US 2006/0229427 A1    Oct. 12, 2006

(30) Foreign Application Priority Data
Aug. 12, 2003 (DE) ............................... 103 37 077

(51) Int. Cl.
*C08G 61/00* (2006.01)
*C08G 61/02* (2006.01)
*C08G 75/00* (2006.01)

(52) U.S. Cl. .................. 525/89; 525/241; 525/133; 525/137; 526/346; 526/103; 528/86; 528/373

(58) Field of Classification Search .......... 528/86, 528/373, 397, 422, 423; 428/690, 917; 252/582; 257/E51.085, E51.051; 525/204, 206, 280, 525/284, 89, 101, 104, 241, 133, 137; 526/103, 526/346
See application file for complete search history.

(56) References Cited

U.S. PATENT DOCUMENTS

| 5,621,131 | A  | * | 4/1997  | Kreuder et al. ............... 558/46 |
| 5,998,045 | A  | * | 12/1999 | Chen et al. .................. 428/690 |
| 6,169,163 | B1 | * | 1/2001  | Woo et al. ................... 528/397 |
| 6,815,505 | B2 | * | 11/2004 | Wu et al. .................... 525/204 |
| 2004/0100804 | A1 | * | 5/2004 | Noguchi et al. ............. 362/555 |
| 2004/0135131 | A1 | * | 7/2004 | Treacher et al. ............ 252/582 |

FOREIGN PATENT DOCUMENTS

| DE | 101 59 946 A1 | 6/2003 |
| EP | 1 398 340 A1 | 3/2004 |
| WO | WO-02077060 A1 * | 10/2002 |
| WO | WO-02088223 A1 * | 11/2002 |
| WO | WO 03/007395 | 1/2003 |

OTHER PUBLICATIONS

Güntner, R. et al., "Conjugated Polyfluorene/Polyaniline Block Copolymers-Improved Synthesis and Nanostructure Formation," *Thin Solid Films*, 417:1-6 (2002).
Chen, X.L. et al., "Block Conjugated Copolymers: Toward Quantum-Well Nanostructures for Exploring Spatial Confinement Effects on Electronic, Optoelectronic, and Optical Phenomena," *Macromolecules*, 29:6189-6192 (1996).

* cited by examiner

*Primary Examiner*—Irina S Zemel
*Assistant Examiner*—Jeffrey Lenihan
(74) *Attorney, Agent, or Firm*—Hamilton, Brook, Smith & Reynolds, P.C.

(57) ABSTRACT

The present invention relates to conjugated copolymers comprising blocks which are linked by random or partly random sections. The materials of the invention display an improved efficiency, a reduced operating voltage and a longer life.

23 Claims, No Drawings

CONJUGATED COPOLYMERS, REPRESENTATION AND USE THEREOF

RELATED APPLICATIONS

This application is the U.S. National Stage of International Application No. PCT/EP2004/009018, filed Aug. 12, 2004, published in German, and claims priority under 35 U.S.C. §365 to German Application No. 103 37 077.3, filed Aug. 12, 2003.

Wide-ranging research on the commercialization of display and lighting elements based on polymer (organic) light-emitting diodes (PLEDs) has been conducted for about 12 years. This development was triggered by the fundamental developments disclosed in EP 423283 (WO 90/13148). Recently, a first, albeit simple, product (a small display in a shaver from PHILIPS N.V.) has also become available on the market. However, significant improvements are still necessary to make these displays genuinely competitive with or superior to the liquid crystal displays (LCDs) which currently dominate the market. In particular, it is necessary to provide polymers for all emission colors (red, green, blue) which satisfy the requirements of the market (efficiency, operating life, operating voltage, to name the most important).

Various classes of materials have been proposed or developed as polymers for full-color displays. Thus, polyfluorene derivatives as disclosed, for example, in EP 0842208, WO 99/54385, WO 00/22027, WO 00/22026 and WO 00/46321, are possibilities. Furthermore, polyspirobifluorene derivatives as disclosed in EP 0707020, EP 0894107 and WO 03/020790 are also possible. Polymers comprising a combination of the two abovementioned structural elements, as disclosed in WO 02/077060 have also been proposed. In general, polymers containing poly-para-phenylene (PPP) as structural element are possible for such use. Apart from the abovementioned classes, further possible polymers are, for example, "ladder PPPs" (LPPPs) (e.g. as described in WO 92/18552), polytetrahydropyrenes (e.g. as described in EP 699699) and also PPPs comprising ansa structures (e.g. as described in EP 690086).

As has already been discovered in some of the abovementioned patent applications, it is necessary to copolymerize particular comonomers into the appropriate polymers in order to produce all three emission colors (cf., for example, WO 00/46321, WO 03/020790 and WO 02/077060). Starting from a blue-emitting base polymer (backbone), it is then possible to produce the two other primary colors red and green.

Furthermore, it has been reported that insertion of particular arylamino groups gives an improvement in the properties: WO 99/54385 and DE 19846767 describe polyfluorenes whose efficiency and operating voltage can be improved by copolymerizing derivatives of triphenylamine, tetraphenyl-p-diaminobenzene, tetraphenyl-4,4'-diaminobiphenyl or substituted diarylamino units into the main chain of the corresponding polymers. WO 01/66618 describes copolymers which comprise not only aryl units but also specific triarylamino or tetraaryl-p-diaminoarylene units in the main chain. The unpublished patent application DE 10304819.7 states that the use of particular carbazole units results in a reduced operating voltage. The unpublished patent application EP 03012409.3 describes the use of oligotriarylamine units.

Despite the advances cited in the abovementioned patent applications, there is still considerable need for improvement for corresponding materials in the following fields:

The operating life, especially in the case of blue-emitting polymers, still requires considerable improvement to enable these to be used for long-lived applications.

The efficiency is still in need of improvement. This is of particularly great importance for mobile applications.

The operating voltage has to be reduced further to enable high brightness to be achieved at sufficiently low voltages in use so that a higher power efficiency is achieved. This is of tremendous importance since it makes it possible, firstly, to achieve the same brightness at a lower energy consumption, which is particularly important in the case of mobile applications (displays for mobile telephones, pagers, PDAs, etc.) which rely on batteries and accummulators, or, secondly, higher brightnesses are achieved at the same energy consumption, which can be of interest for, for example, lighting applications.

Copolymers of two or more different monomers can in principle have various structures:

In alternating copolymers, the two (or three or more) repeating units alternate.

In random copolymers, the sequence of the building blocks is determined by the laws of probability applicable in the polymerization.

In partly random copolymers in the context of the present invention, the arrangement of one of the repeating units is defined, while the other repeating units are arranged randomly. Such copolymers are, for example, obtained by reaction of a monomer A with two monomers B and B', with both B and B' being able to react only with A but not with B or B'.

Block copolymers consist of blocks of homo sequences or of blocks of defined sequences which are linked to one another via the ends. The blocks can also be linked via elements in the middle of the chain. In this case, graft copolymers are obtained.

Different structural features of these types can also be combined in a polymer. Thus, for example, blocks can be linked via random or partly random sequences ("tapered copolymer").

WO 00/55927 describes copolymers which comprise two or more regions in the polymer backbone. Here, the first region serves for the transport of negative charge carriers, the second region serves for the transport of positive charge carriers, while in the third region positive and negative charge carriers recombine with generation of light. The term "region" in the present context refers to a segment of the polymer chain which can consist of one or more monomers. The arrangement and ratio of the monomers in the polymer are selected so that the band gaps of the individual regions in the polymer are different. It is stated that the individual components in the main chain and in the side chain can be combined as block copolymers or as random polymers. However, only the synthesis of random or alternating copolymers is described, and only partly random or alternating copolymers but no block copolymers are presented in the examples. No advantage of block copolymers over random polymers is mentioned either, so that it is not obvious how usable block polymers can be prepared, and it is obvious to presume that block copolymers are referred to only coincidentally here.

EP 1149827 describes polyfluorenes having a block structure of the general composition

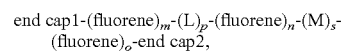

end cap1-(fluorene)$_m$-(L)$_p$-(fluorene)$_n$-(M)$_s$-(fluorene)$_o$-end cap2, where L and M are any aromatic monomers, with the proviso that m+n+o≧10, p and s are each in the range from 0 to 15 and at least one of the two end caps displays charge transport properties. Particular advantages of such a polymer having block-like substructures are not mentioned. In addition, no example of such a block polymer is given, nor is any synthetic method suitable for preparing it, and polymers in which m, p, s and o=0, i.e. have only fluorene units and thus are not block copolymers, are named as preferred structures. It can therefore be presumed that the block structure is mentioned only coincidentally here. In particular, the way in which such block polymers can be synthesized will not be clear to a person skilled in the art, since polycondensation processes as are customarily employed for this type of polymers and are also mentioned in the examples always lead to mixtures and not to clearly defined polymers which have precisely three oligofluorene segments which are linked via two (oligo)aromatic segments.

WO 02/088223 describes the synthesis and use of conjugated block copolymers comprising two or more blocks which may be identical or different and can have one or more repeating units and can be joined to one another either directly or via an intermediate unit.

WO 03/007395 describes conjugated block copolymers which comprise an emitter block and at least one further block which can be a charge transport block or a host polymer block. Advantages indicated for these polymers are that they display better properties in electroluminescence devices compared to random copolymers or blends of random polymers, in particular in respect of the brightness, the power efficiency and the life. However, only polymers whose blocks are partly random or alternating are given as examples. Homoblocks or random sections are not described. If the block copolymers are compared with the partly random polymers reported in the comparative examples, the block copolymers actually do appear to display a higher efficiency (1.3 cd/A@ 100 cd/m$^2$ vs. 0.4 cd/A@ 100 cd/m$^2$) and a longer life (50 h vs. <1 min.). However, these data presented here cannot be considered significant since far better polymers, both in respect of the efficiency and in respect of the life, were known at the point in time of the invention: S. J. M. O'Connor et al. (*Proceedings of SPIE* 2001, 4105, 9-17) indicate, for example, an efficiency of 1.43 cd/A at 100 cd/m$^2$ and a life of 1600 h at 100 cd/m$^2$ for a blue polymer. An advantage given by the introduction of block structures is thus not apparent.

The properties of known polymers in electroluminescence devices have thus, as described, undergone significant further development in recent years. However, as can be seen from the description of the prior art, there is still a great need for further development in the field of light-emitting polymers, since, in particular, the operating life, especially for blue-emitting polymers, the efficiency and the operating voltage do not yet meet the prerequisites which will enable the polymers to be incorporated in high-quality full color displays.

We have now surprisingly found that particular conjugated polymers in which ordered blocks are linked to polymer sections which do not have a block structure display significant improvements, specifically in the abovementioned area, i.e. the operating life, the efficiency and the operating voltage. These are therefore subject matter of the present invention.

The invention provides conjugated copolymers comprising at least one block structure which has at least one of the following properties:
a) charge transport block (either for hole transport or electron transport), or
b) charge injection block (either for the injection of positive charges or the injection of negative charges), or
c) emitting block, or
d) block which aids the transition from singlet excitons to triplet excitons, or
e) polymer backbone block, characterized in that these block structures are linked by random or partly random polymer sections.

Even though this is indicated by the above description, it will at this point once more be explicitly stated that the copolymers can comprise a plurality of different block structures as described above and in a) to e).

In a preferred embodiment of the invention, the random or partly random polymer sections are made up of at least four different monomers.

For the purposes of the present invention, a block is quite generally a polymer section which has a defined monomer sequence. This block can either be made up of alternating structures, in the simplest case A-B-A-B in the case of only two different monomers, or it can be a homoblock which consists of only one type of monomer. For the purposes of the present invention, a block is therefore not a polymer section which has a random or partly random monomer sequence.

In a preferred embodiment of the invention, the blocks have alternating sequences of repeating units.

In a further preferred embodiment of the invention, the blocks have homo sequences.

For the purposes of the present invention, a random polymer section is a polymer section in which the sequence of all building blocks is determined by the laws of probability applicable in the polymerization. For the purposes of the present invention, a partly random polymer section is a polymer section in which the arrangement of one of the repeating units is defined, while the other repeating units are arranged randomly. Such sections are, for example, obtained by reaction of a monomer A with two monomers B and B' when both B and B' can react only with A but not with B or B'.

Preference is given to at least one of these blocks being a block which makes hole transport, electron transport, the transition from singlet excitons to triplet excitons or emission of light possible. It is possible for one block to simultaneously have one or more of these properties.

In a particularly preferred embodiment, the polymer comprises hole conductor homoblocks.

In a further particularly preferred embodiment, the polymer comprises alternating hole conductor-backbone blocks.

In a further particularly preferred embodiment, the polymer comprises emitter homoblocks.

In a further particularly preferred embodiment, the polymer comprises alternating emitter-backbone blocks.

In a further particularly preferred embodiment, the polymer comprises a plurality of blocks which comprise a plurality of different block structures, for example alternating hole conductor-backbone blocks and alternating emitter-backbone blocks, which are linked by random or partly random sequences or individual monomers.

In a further particularly preferred embodiment, the polymer comprises a plurality of different block structures which are linked directly to one another by means of stepwise construction.

The proportion of monomers present in blocks in the polymer is at least 1 mol %, preferably at least 5 mol %, particularly preferably at least 10 mol %. Such a proportion has been found to be particularly advantageous when the polymers are used as electroluminescence materials. Moreover, a significantly higher proportion of blocks can be preferred for other applications, for example a proportion of charge transport blocks of 50 mol % and more when the polymer is used in organic field effect transistors (O-FETs).

Furthermore, particularly good results are obtained when the blocks have a molecular weight $M_w$ of from $10^3$-$3\times 10^5$ g/mol, preferably from $3\times 10^3$ to $10^5$ g/mol, particularly preferably from $5\times 10^3$ to $8\times 10^4$ g/mol.

The proportion of monomers which is present in random or partly random sections in the polymer is at least 1 mol %, preferably at least 5 mol %, particularly preferably at least 10 mol %, in particular at least 30 mol %.

Furthermore, the random or partly random polymer sections have an average of at least 2 repeating units, preferably at least 5 repeating units, particularly preferably at least 10 repeating units.

For the purposes of the present invention, a conjugated polymer is a polymer which comprises mainly $sp^2$-hybridized carbon atoms, which may also be replaced by corresponding heteroatoms, in the main chain. In the simplest case, this means the alternating presence of double (or triple) and single bonds in the main chain. "Mainly" means that naturally occurring defects which lead to interruptions to conjugation do not invalidate the term "conjugated polymers". For the purposes of the present invention, polymers are likewise referred to as conjugated if, for example, arylamine units and/or particular heterocycles (i.e. conjugation via N, O or S atoms) and/or organic metal complexes (i.e. conjugation via the metal atom) are present in the main chain.

On the other hand, units such as simple or (thio)ether bridges, alkylene chains, ester, amide or imide linkages are unambiguously defined as nonconjugated segments.

The copolymers of the invention can comprise various structural elements. These are, inter alia, ones which have been disclosed in the abovementioned patent applications. Reference may here be made, in particular, to the relatively comprehensive listing in the abovementioned patent application WO 02/077060; this is incorporated by reference into the present invention. These further structural units can, for example, come from the classes described below:

1. Structural units which form the polymer backbone, or blue-emitting units:

Mention may here firstly be made of polyphenylenes and units forming structures derived therefrom. These are, for example (in each case substituted or unsubstituted) meta- or para-phenylenes, 1,4-naphthylenes, 9,10-anthracenylenes, 2,7-phenanthrenylenes, 2,7-(9,10-dihydro)phenanthrenylenes, 1,6- or 2,7- or 4,9-pyrenes or 2,7-tetrahydropyrenes. Corresponding structures forming heterocyclic "polyarylenes", for example oxadiazolylenes, 2,5-thiophenylenes, 2,5-pyrrolylenes, 2,5-furanylenes, 2,5-pyridylenes, 2,5-pyrimidinylenes, 3,6- or 2,7-carbazolylenes or 5,8-quinolinylenes, are also possible.

Furthermore, more complex units such as the abovementioned fluorenes, spiro-9,9'-bifluorenes, multiply bridged units (e.g. short subsegments of the abovementioned L-PPP polymers) and also "double" fluorene units (cis- or trans-indenofluorenes) are also possible. These, too, can be substituted or unsubstituted.

Preferred units are spiro-9,9'-bifluorenes, fluorenes, indenofluorenes and dihydrophenanthrenes.

2. Structural units which influence the charge injection or charge transport properties:

This can relate either to the electron injection or transport properties (for example oxadiazole units) or the hole injection or transport properties (for example triarylamine units). Here, reference may once again be made to the comprehensive listing of such structural units in the above-cited patent application WO 02/077060. Naphthylarylamines (WO 04/037887) or carbazole units (DE 10304819.7) are likewise possible for this purpose.

3. Structural units which shift the color of the emission, thus also alter the band gap of the polymer and therefore generally also alter the charge injection or transport properties:

Mention may here be made of, for example, heterocyclic compounds such as the structures mentioned in the abovementioned patent application WO 03/020790 under the formulae (XX) to (XXXXVI).

Furthermore, mention may here also be made of arylene-vinylene or arylene-acetylene structures, e.g. substituted or unsubstituted stilbenylenes, tolanylenes, bisstyrylarylenes, bis(arylacetylene)arylenes.

Finally, the incorporation of relatively large aromatic units, for example chrysenes, naphthacenes, pyrenes, pentacenes, perylenes or coronenes, can also produce the abovementioned effect (color shift).

4. Structural units which make the transfer of singlet excitons to triplet excitons possible and which can emit light with high efficiency from the triplet state even at room temperature:

These are, first and foremost, compounds which comprise heavy atoms, i.e. atoms from the Periodic Table of the Elements having an atomic number of more than 36.

Compounds comprising d and f transition metals which meet the abovementioned condition are particularly useful for this purpose. Corresponding structural units comprising elements of groups 8 to 10 (i.e. Ru, Os, Rh, Ir, Pd, Pt) appear to be very particularly preferred here.

Here, various complexes, for example those described in the patent applications WO 02/068435, DE 10116962, EP 1239526 and WO 04/026886, are possible as structural units for the polymers of the invention.

Furthermore, it can be useful to use further components which aid singlet-triplet transfer in addition to the abovementioned compounds which can emit light from the triplet state. Compounds which can be used for this purpose are, for example, carbazoles (DE 10304819.7) or carbazole dimers (DE 10328627.6).

A selection of preferred further units of the polymers of the invention are listed in the following overview. The single bond symbolizes the linkage in the polymer. It does not indicate a methyl group.

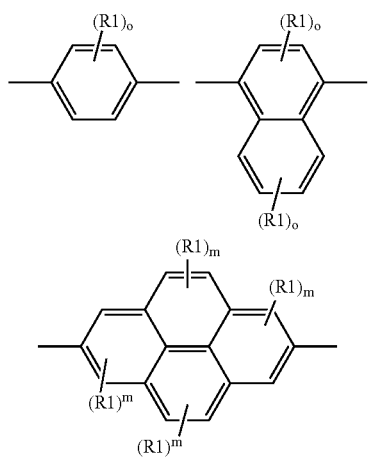

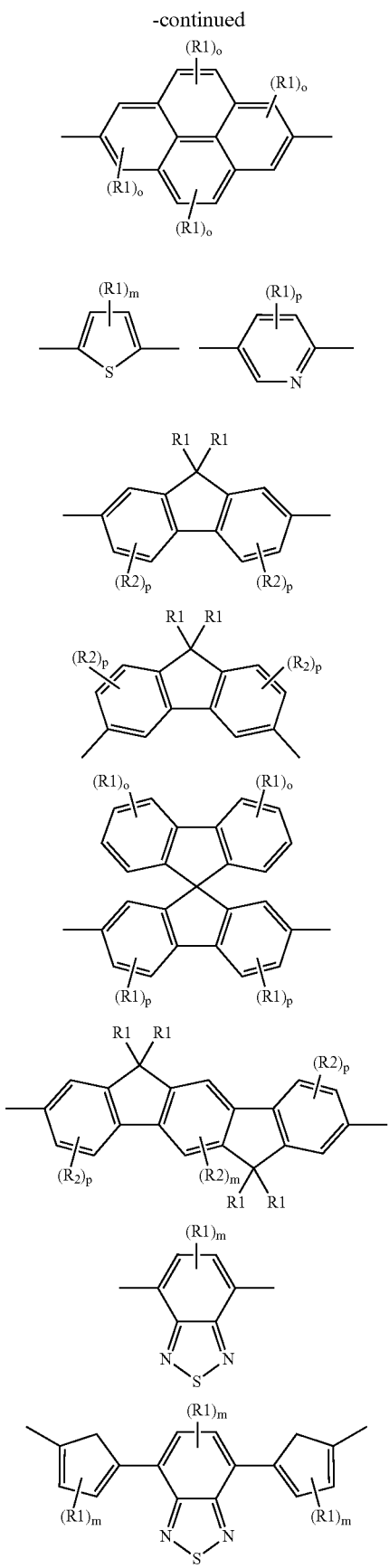

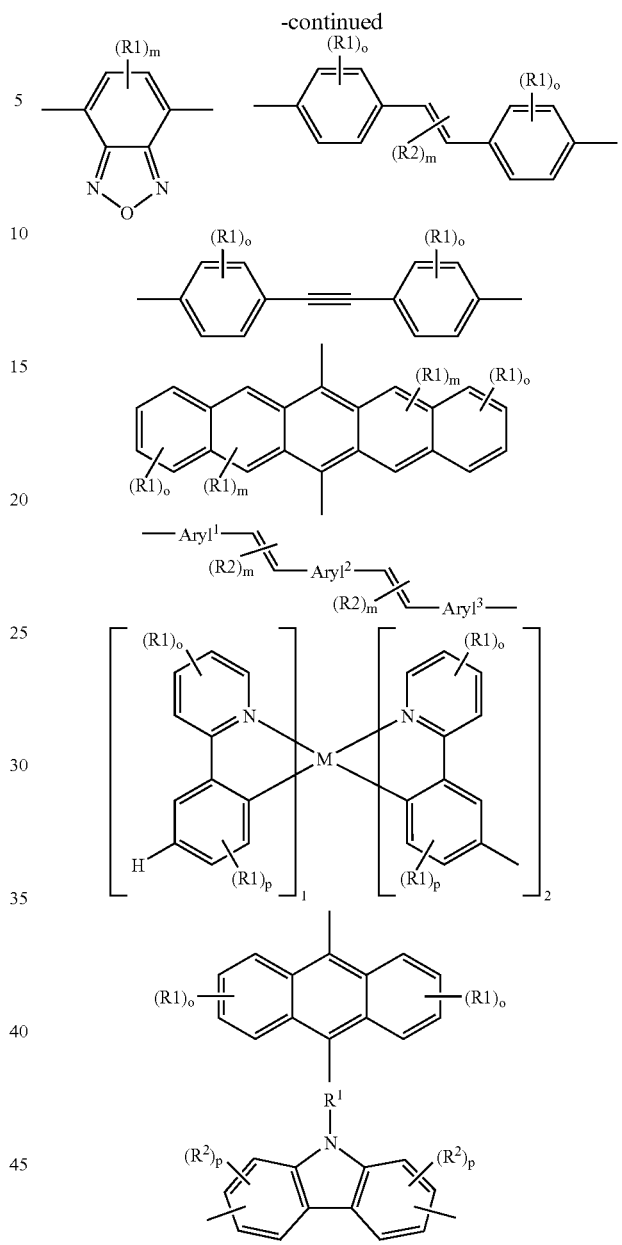

Here, the symbols R1, R2, Aryl¹, Aryl², Aryl³, M and indices m, o and p have the following meanings:

Aryl¹, Aryl³ are identical or different on each occurrence and are each an aromatic or heteroaromatic ring system which has from 2 to 40 carbon atoms and may be substituted or unsubstituted; with the possible substituents R1 being potentially able to be located at any free position;

Aryl² is identical or different on each occurrence and is in each case Aryl¹, Aryl³ or a substituted or unsubstituted stilbenylene or tolanylene unit;

R1 is identical or different on each occurrence and is in each case a straight-chain, branched or cyclic alkyl or alkoxy chain having from 1 to 22 carbon atoms in which one or more nonadjacent carbon atoms may also be replaced by NR2, O, S, CO—O, O—CO—O and one or more H atoms may also be replaced by fluorine, an aryl or aryloxy group having from 5 to 40 carbon atoms in which one or more carbon atoms may also be replaced by O, S or N, which may also be substituted by one or more nonaromatic radicals R1, or Cl, F, CN, $N(R2)_2$, $B(R2)_2$ with two or more radicals R1 together also being able to form a ring system;

R2 is identical or different on each occurrence and is in each case H, a straight-chain, branched or cyclic alkyl chain having from 1 to 22 carbon atoms in which one or more nonadjacent carbon atoms may also be replaced by O, S, CO—O, O—CO—O and one or more H atoms may also be replaced by fluorine, an aryl group having from 5 to 40 carbon atoms in which one or more carbon atoms may also be replaced by O, S or N, which may also be substituted by one or more nonaromatic radicals R1;

m is identical or different on each occurrence and is in each case 0, 1 or 2;

o is identical or different on each occurrence and is in each case 0, 1, 2, 3 or 4;

p is identical or different on each occurrence and is in each case 0, 1, 2 or 3;

M is identical or different on each occurrence and is in each case Rh or Ir.

The polymers of the invention generally have from 10 to 10,000, preferably from 50 to 5000, particularly preferably from 50 to 2000, repeating units.

The necessary solubility is achieved first and foremost by means of the substituents R1. It is therefore generally necessary for an average of at least 2 nonaromatic carbon atoms being present in the substituents per repeating unit. Preference is given to at least 4, particularly preferably at least 8, carbon atoms. Some of these carbon atoms can also be replaced by O or S. This does not rule out a situation in which a proportion of repeating units bears no further nonaromatic substituents. To avoid adversely affecting the morphology of the film, preference is given to no long-chain substituents having more than 12 carbon atoms in a linear chain being present, preferably no substituents having more than 8 carbon atoms, particularly preferably no substituents having more than 6 carbon atoms.

Nonaromatic carbon atoms are, as stated in the description of R1, present in appropriate straight-chain, branched or cyclic alkyl or alkoxy chains.

The copolymers of the invention preferably comprise at least one type of blocks having an alternating monomer sequence or a homo sequence, with the blocks being able to be blocked which influence hole injection or hole transport, electron injection or electron transport, the transition from single excitons to triplet excitons or emission of light. Here, one block can also simultaneously have a plurality of properties. These blocks having a defined sequence are linked via polymer sections having a random or partly random sequence. The use of both defined blocks and random polymer sections in the same copolymer enables properties such as solubility, solid state morphology, charge transport properties, etc., to be adjusted and thus allows the emission properties of the polymer to be significantly improved. This is, in particular, the case when four or more different monomers are used for the random polymer sections.

Particularly preferred copolymers comprise at least one type of charged transport block which is either made up of alternating units of a polymer backbone having a charge transport unit or of only charge transport units, with the blocks being linked to one another via random or partly random sections. The preferred molecular weight $M_w$ of the blocks is in the range $5 \times 10^3$-$8 \times 10^4$.

The copolymers of the invention are generally prepared by polymerization of one or more monomers. There are in principle a relatively large number of appropriate polymerization reactions which are suitable for this purpose; however, the polycondensation reactions listed below have been found to be particularly useful. Basically reaction types (A) to (C) give C-C linkages, while reaction type (D) gives C-N linkages:

(A) SUZUKI polymerization (B) YAMAMOTO polymerization (C) STILLE polymerization (D) HARTWIG-BUCHWALD polymerization These methods are described in detail in, for example, WO 03/048225 and WO 04/022626 and the references cited therein. They are incorporated by reference into the present patent application.

The actual polymerization (polycondensation) (cf. the details in the examples) proceeds in two (or more) steps. Firstly, the part of the monomers which are to form the block are generally reacted in a suitable concentration range in solution with the appropriate catalysts and auxiliary systems. If only one type of repeating units is used, homoblocks are formed in this way. To obtain an alternating sequence in the block, use can be made, for example, of the characteristic property of the polymerization processes (A), (C) and (D) that the monomers can react not only with themselves but also with monomers having other functional groups. The size of the blocks can be controlled, for example, by deviation from 1:1 stoichiometry for the different monomers, but also by means of the reaction time before addition of further monomers. When the block has reached the desired size, the remaining monomers, if appropriate together with further solvent, catalyst and further auxiliary systems, are added and the polymerization is continued. Here, it can be advantageous to restrict the molecular weight by means of small deviations from ideal stoichiometry or by means of the presence of small amounts of monofunctional compounds. The reaction is generally carried out to the desired molecular weight (the process can be monitored by means of, for example, viscosity measurements, etc.). However, it is also possible to build up further blocks different from the first block and then to link these via the random or partly random sections. It is likewise possible to commence the polymerization with the random or partly random section and then to build up the blocks, as described above, only subsequently. Furthermore, it is likewise possible to prepolymerize the blocks and the random or partly random sections separately and subsequently to polymerize the polymer further by forming a smaller number of fresh bonds between the blocks and the random or partly random sections. The reaction is then stopped. This can be carried out in various ways. To avoid reactive end groups, it has been found to be useful to carry out "end capping", i.e. to add monofunctional compounds after the desired molecular weight has been reached. In the case of reaction types A, C and D, this can also be carried out in a double fashion, i.e. one or more monofunctional compound(s) of one type (e.g. monohalide) is/are added first and a compound of the other type (e.g. monoboronic acid derivative) is subsequently added.

The copolymers which have been synthesized then firstly have to be separated off from the reaction medium. Isolation and purification of the polymers obtained in this way has been described in detail in, for example, WO 04/037887 and will not be discussed again at this point.

To be able to prepare the polymers of the invention, for example by means of the processes described, the corresponding monomers are used. The synthesis leading to the structures as have been described above is described in detail in the abovementioned patent applications and patents. A good overview is given by the patent application WO 02/077060; the information given there is incorporated by reference into the present patent application. To obtain homoblocks of triarylamine units, the corresponding dihalides and also the corresponding boronic acid derivatives are required for the polymerization process (A). For the fully random polymers, too, both the halides and the corresponding boronic acid derivatives of all monomers are required.

Boronic acid derivatives of triarylamine units can be obtained, for example, by reaction of the corresponding dihalide compound with an alkyllithium compound, followed by reaction with triisopropyl borate. The reaction to form the Grignard reagent followed by reaction with triisopropyl borate is also possible.

Another possible synthetic route is reaction of the corresponding dihalides with diborates or boranes in the presence of a palladium catalyst. This is a good alternative to the above synthesis when the substances concerned are sensitive to bases and cannot be lithiated or converted into the Grignard reagent, or cannot be lithiated selectively or converted into the Grignard reagent selectively.

A further possible way of obtaining the appropriate boronic acid derivatives starts out from primary or secondary arylamine compounds. These can then be reacted with an aryl monohalide monoboronic ester compound in a HARTWIG-BUCHWALD coupling reaction under the reaction conditions known to those skilled in the art.

The boronic acids or boronic acid derivatives obtained in this way can, if desired, be converted further into other boronic esters by esterification or transesterification. This can bring advantages in use since the boronic esters can be purified more easily as a result of different solubility properties. The fact that different boronic esters have different stabilities and reactivities is also of interest.

The direct reaction of primary or secondary arylamines with aryl monohalide monoboronic ester compounds in which the halide function reacts while retaining the boronic ester function is unexpected and novel.

The invention thus also provides a process as shown in formula (I) for preparing arylamine- or (heteroaryl)amine-boronic acid derivatives by HARTWIG-BUCHWALD coupling of a primary or secondary amine in the presence of a palladium compound, at least one phosphine ligand and a base, characterized in that the reaction with an aryl or heteroaryl monohalide monoboronic ester compound or with an aryl or heteroaryl monosulfonate monoboronic ester compound is carried out:

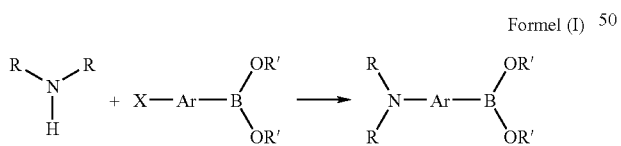

Formel (I)

[Formel=formula]

where the following applies to the symbols used:

R is identical or different on each occurrence and is in each case H, a straight-chain, branched or cyclic alkyl chain having from 1 to 22 carbon atoms in which one or more nonadjacent carbon atoms may also be replaced by N—R'', O, S, CO—O, O—CO—O and one or more H atoms may also be replaced by fluorine, an aryl or heteroaryl group having from 5 to 40 carbon atoms in which one or more carbon atoms may also be replaced by O, S or N and which may also be substituted by one or more nonaromatic radicals R, where two or more of the radicals R together may also form a ring system, with the proviso that at least one of the radicals R in the starting compound is not H;

R' is identical or different on each occurrence and is in each case H, a straight-chain, branched or cyclic alkyl chain having from 1 to 22 carbon atoms in which one or more nonadjacent carbon atoms may also be replaced by O, S, CO—O, O—CO—O and one or more H atoms may also be replaced by fluorine, an aryl or heteroaryl group having from 5 to 40 carbon atoms in which one or more carbon atoms may also be replaced by O, S or N and which may be substituted by one or more nonaromatic radicals R, where one or more radicals R' together may also form a ring system;

X is identical or different on each occurrence and is in each case Cl, Br, I or O—$SO_2$R', with the proviso that R' is in this case not H;

Ar is identical or different on each occurrence and is in each case an arylene or heteroarylene group having from 5 to 40 carbon atoms in which one or more carbon atoms may also be replaced by O, S or N, which may also be substituted by one or more radicals R'.

This synthesis according to the formula (I) can, for example, be used for the synthesis of tetraphenylbenzidine substituted by a boronic ester, as shown in formula (II):

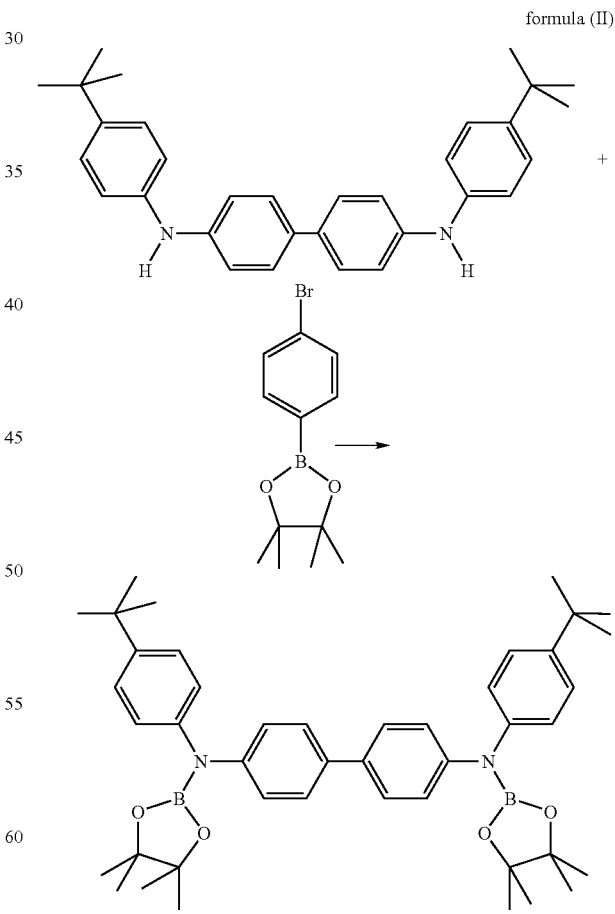

formula (II)

In addition, it can be preferable to use the copolymer of the invention not as a pure substance but instead as a mixture (blend) together with any further desired polymeric, oligomeric, dendritic or low molecular weight substances. These can, for example, improve the electronic properties, influence the transfer from the singlet state to the triplet state or themselves be emitters. However, electronically inactive substances can also be appropriate, for example to influence the morphology of the polymer film formed or to influence the viscosity of polymer solutions. Such blends are therefore also provided by the present invention.

The invention further provides solutions of one or more polymers or blends according to the invention in one or more solvents. The way in which polymer solutions can be prepared is described, for example, in WO 02/072714, WO 03/019694 and the references cited therein. The solutions can be used to produce thin polymer layers, for example by area coating processes (e.g. spin coating) or by printing processes (e.g. ink jet printing).

The polymers of the invention have, inter alia, the following surprising advantages over the abovementioned prior art:
  The operating life when used in PLEDs is significantly increased for comparable polymers (cf. data in Table 1). This is the case especially when charge transport homoblocks are used. This brings significant advantages in use, since the objective of producing long-lived full color displays has moved closer.
  The efficiency can be increased significantly for comparable polymers if these comprise both ordered blocks and random or partly random sections composed of at least four different monomers. This effect is likewise particularly pronounced in the case of charge transport homoblocks. This can be seen from the data in Table 1.
  The operating voltage for use in PLEDs can be reduced significantly when the polymer comprises suitable charge transport blocks. The results here are particularly good when the charge transport units alternate with polymer backbone units in the block.
  Copolymers of this type can be built up so that they can emit all primary colors (red, green, blue).
  The solubility in organic solvents is generally good, i.e. the polymers are soluble in amounts in the range from 1 to about 30 g/l (depending on the type of block and the molecular weight of the polymer) in solvents such as toluene, xylene, anisole, methylanisole, methylnaphthalene.

Although the last two points bring no improvement over known materials, it is essential that these properties are also retained in polymers according to the invention.

The copolymers of the invention can be used in PLEDs. The way in which PLEDs can be produced is described comprehensively as a general process in WO 04/037887, and this can be adapted appropriately for the individual case. As described above, the copolymers of the invention are very particularly useful as electroluminescence materials in the PLEDs or displays produced in this way.

For the purposes of the invention, electroluminescence materials are materials which can be used as active layer in a PLED. "Active layer" means that the layer is capable of radiating light on application of an electric field (light-emitting layer) and/or that it improves the injection and/or transport of the positive and/or negative charges (charge injection or charge transport layer).

The invention therefore also provides for the use of a copolymer according to the invention in organic electronic devices, e.g. in polymeric light-emitting diodes (PLEDs), organic field effect transistors (O-FETs), organic integrated circuits (O-ICs), organic thin film transistors (O-TFTs), organic solar cells (O-SCs), organic laser diodes (O-lasers) and for nonlinear optics, but in particular as electroluminescence material.

The invention thus likewise provides an electronic device, e.g. a polymeric light-emitting diode (PLED), an organic field effect transistor (O-FET), an organic integrated circuit (O-IC), an organic thin film transistor (O-TFT), an organic solar cell (O-SC), an organic laser diode (O-laser) or a device for nonlinear optics, but in particular a polymeric light-emitting diode (PLED) having one or more active layers of which at least one comprises one or more copolymers according to the invention. The active layer can be, for example, a light-emitting layer and/or a charge transport layer and/or a charge injection layer.

The present patent application text and also the further examples below are directed predominantly at the use of copolymers according to the invention for PLEDs and the corresponding displays. Despite this restriction of the description, a person skilled in the art will be able, without making a further inventive step, to utilize the polymers of the invention for further applications in other electronic devices, e.g. O-ICs, OFETs, OTFTs, O-SCs, O-lasers or nonlinear optics, to name only a few applications. O-ICs and OFETs, in particular, can be produced using appropriate copolymers according to the invention which have a relatively high proportion of charge transport homoblocks or alternating charge transport blocks.

The invention is illustrated by the following examples without being restricted thereby.

EXAMPLES

Part A: Synthesis of the Monomers

A1: Synthesis of Boronic Ester Monomers (Required for the Synthesis of Blocks or Random Polymers)

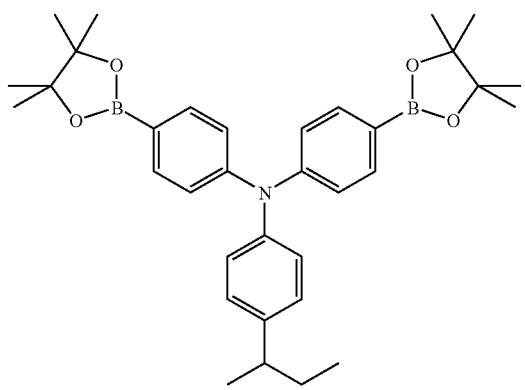

A1.1 Synthesis of N,N-bis(4-boronic acid pinacol ester)phenyl-N-(4-tert-butylphenyl)amine (BOR1)

In a baked 5 l four-necked flask provided with mechanical stirrer, nitrogen connection, dropping funnel and low-temperature thermometer, 150 g (327 mmol) of monomer M11 (substituted by a sec-butyl group) were dissolved in 2.5 l of dry THF and cooled to −78° C. 390 ml (975 mmol) of butyl-lithium (2.5 molar solution in hexane) were added dropwise to the reaction mixture in such a way that the internal temperature did not exceed −70° C. After the addition was complete, the mixture was stirred at −78° C. for another 45 minutes. 230 ml (991 mmol) of triisopropyl borate were then added dropwise in such a way that the internal temperature did not exceed −70° C. The mixture was stirred at −78° C. for another 4 hours, after which 500 ml of HCl (2 molar solution in diethyl ether) were added at −70° C. and the mixture was then allowed to come to room temperature. The product was evaporated under reduced pressure. The residue was taken up in 1 l of toluene and the precipitated LiBr was filtered off. 112 g (950 mmol) of pinacol and 1 g of para-toluenesulfonic acid were added and the reaction mixture was refluxed on a water separator for 2 hours. After cooling to room temperature, 3 g of potassium carbonate were added, the mixture was filtered and evaporated under reduced pressure. The product was stirred with 200 ml of ethyl acetate for 1 hour, filtered and dried overnight at 40° C. under reduced pressure. The pure product was obtained by repeated recrystallization from ethyl acetate. This gave 45.2 g (25% of theory) of the product in a purity of 100% (according to HPLC and GC/MS).

$^1$H-NMR (500 MHz, CDCl$_3$): 0.84 (t, J=7.4 Hz, 3H, CH$_3$), 1.23 (d, J=7 Hz, 3H, CH$_3$), 1.33 (s, 24H, pinacol) 1.57 (m, 2H, CH$_2$), 2.57 (m, 1H, CH), 7.04 (m, 8H, phenylene), 7.66 (m, 4H, phenylene).

A1.2 Synthesis of Monomer BOR2

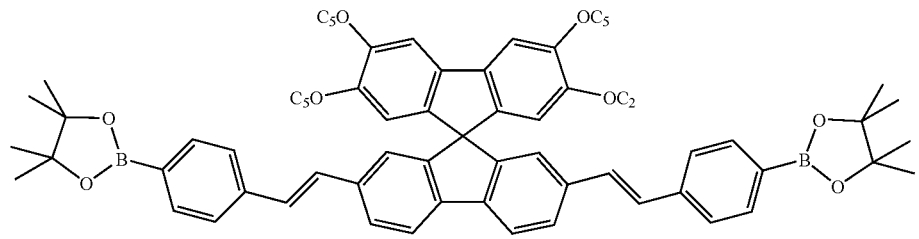

20.46 g (20 mmol) of monomer M19 together with 520 ml of dioxane were placed in a reaction vessel. 20 ml (144 mmol) of triethylamine, 9.9 ml (68 mmol) of pinacolborane and subsequently 1 g (1.36 mmol) of [1,1-bis(diphenylphosphino)ferrocenyl]palladium(II) chloride were added and the mixture was heated at 80° C. under argon for 72 hours. The dioxane was removed under reduced pressure. The residue was taken up in 500 ml of ethyl acetate and 500 ml of water and filtered. The phases were separated and the aqueous phase was extracted with 3×150 ml of ethyl acetate. The combined organic phases were dried over MgSO$_4$ and the solvent was removed under reduced pressure. The crude product was stirred with hexane, filtered and dried. Further purification was effected by repeated crystallization from dioxane. This gave 9.37 g (42% of theory) of product in a purity of 99.7% (according to HPLC).

$^1$H-NMR (CDCl$_3$, 500 MHz): 0.86 (t, $^3J_{HH}$=7.5 Hz, 6H, CH$_3$), 0.93 (d, $^3J_{HH}$=9.7 Hz, 6H, CH$_3$), 0.99 (t, $^3J_{HH}$=7.3 Hz, 6H, CH$_3$), 1.09 (d, $^3J_{HH}$=6.7 Hz, 6H, CH$_3$), 1.18 (m, 2H, CH$_2$), 1.34 (m, 2H, CH$_2$), 1.36 (s, 24H, CH$_3$), 1.48 (m, 2H, CH), 1.64 (m, 2H, CH), 1.75 (m, 2H, CH$_2$), 1.95 (m, 2H, CH$_2$), 3.55 (m, 4H, CH$_2$), 3.95 (m, 4H, CH$_2$), 6.20 (s, 2H, spiro), 6.88 (s, 2H, spiro), 6.91 (2 d, $^3J_{HH}$=16.1 Hz, 4H, olefin), 7.26 (m, 2H, spiro), 7.72 (d, $^3J_{HH}$=9.0 Hz, 4H, phenylene), 7.49 (dd, $^3J_{HH}$=8.0 Hz, $^4J_{HH}$=1.4 Hz, 2H, spiro), 7.55 (d, $^3J_{HH}$=8.9 Hz, 4H, phenylene), 7.78 (d, $^3J_{HH}$=7.7 HZ, 2H, spiro).

A1.3 Synthesis of N,N'-bis(4-boronic acid pinacol ester)phenyl-N,N'-bis(4-tert-butylphenyl)biphenyl-4,4'-diamine (BOR3)

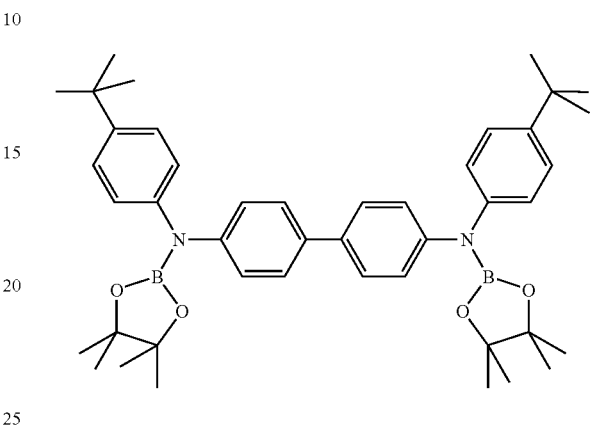

A degassed solution of 8.75 g (19.5 mmol) of N,N'-bis(4-tert-butylphenyl)biphenyl-4,4'-diamine and 12.11 g (42.8 mmol) of 1-bromo-4-(pinacolborane)benzene in 500 ml of toluene was saturated with N$_2$ for 1 hour. The solution was then admixed with 157.8 mg (0.78 mmol) of P($^t$Bu)$_3$ and 87.6 mg (0.39 mmol) of Pd(OAc)$_2$, and 4.84 g (50.4 mmol) of solid NaO$^t$Bu were subsequently added. The reaction mixture was refluxed for 4 hours. After cooling to room temperature, 153 mg of NaCN and 10 ml of water were carefully added. The organic phase was washed with 4×50 ml of H$_2$O, dried over MgSO$_4$ and the solvents were removed under reduced pressure. The pure product was obtained by recrystallization from dioxane. The yield was 6.6 g (40% of theory), and the purity was 99.8% (according to HPLC).

$^1$H-NMR (CDCl$_3$, 500 MHz): 1.32 (s, 18H), 1.33 (s, 24H), 7.05 (d, J=8.7 Hz, 8H), 7.13 (d, J=8.7 Hz, 4H), 7.27 (d, J=8.4 Hz, 4H), 7.45 (d, J=8.4 Hz, 4H), 7.66 (d, J=8.7 Hz, 4H).

A2: Monomers for Further Units

The synthesis of the further monomers M1 to M23 has been described in detail in WO 02/077060 and the references cited therein. The monomers are shown once again below to give a better overview:

-continued
M1
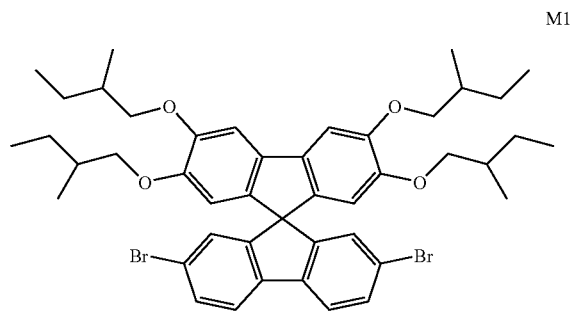
M2
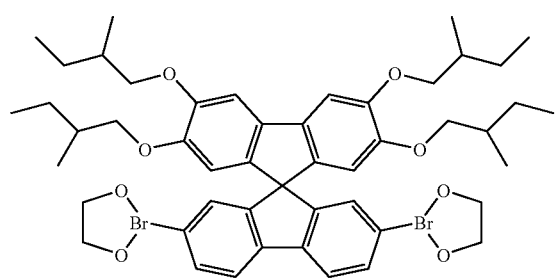
M3
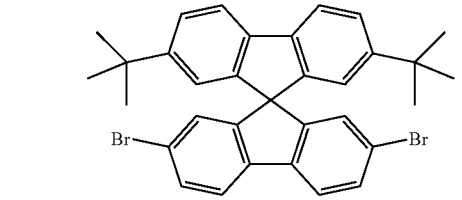
M4
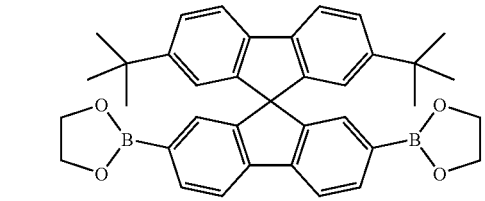
M5
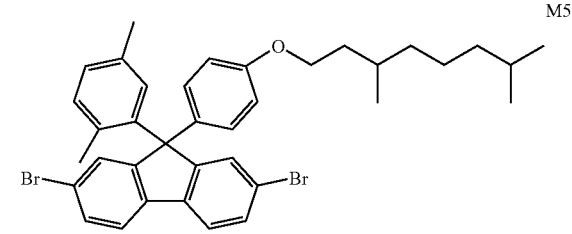
M6
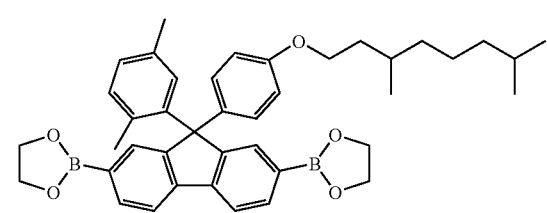
M7
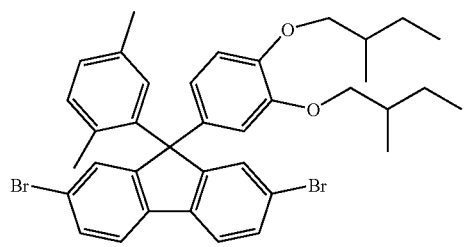
M8
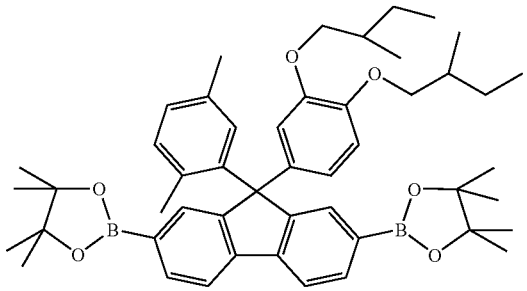
M9
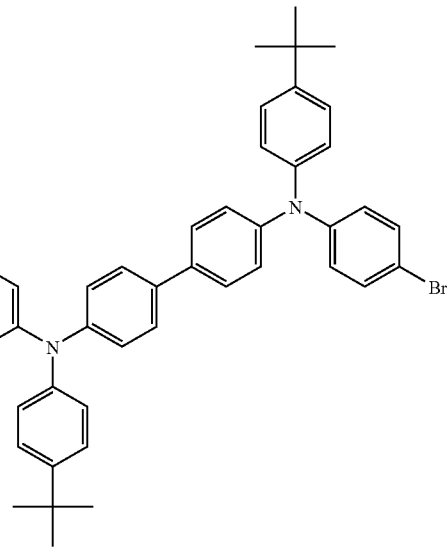
M10
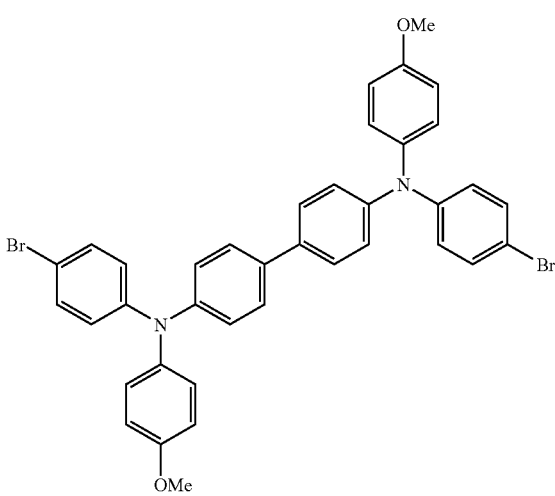

-continued
M11
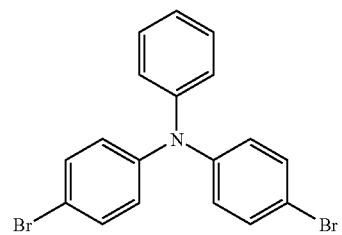
M12
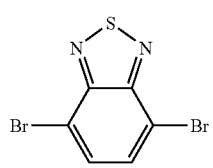
M13
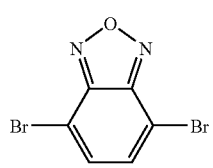
M14
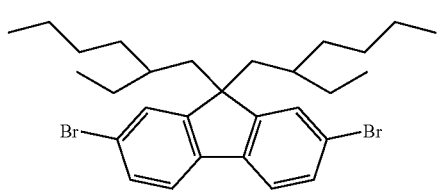
M15
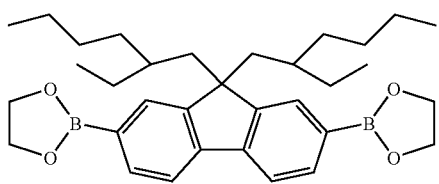
M16
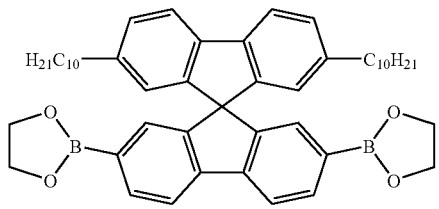
M17
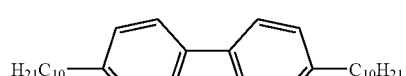
M18
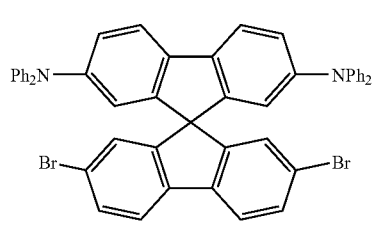
-continued
M19
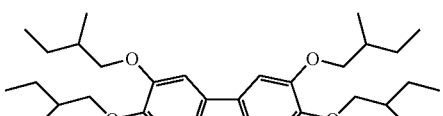
M20
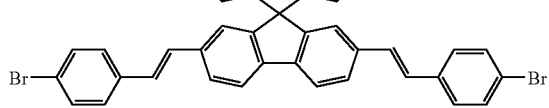
M21
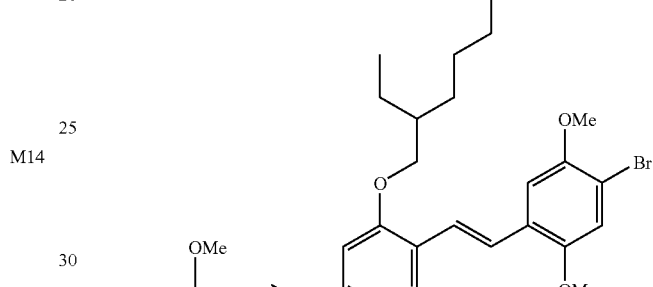
M22
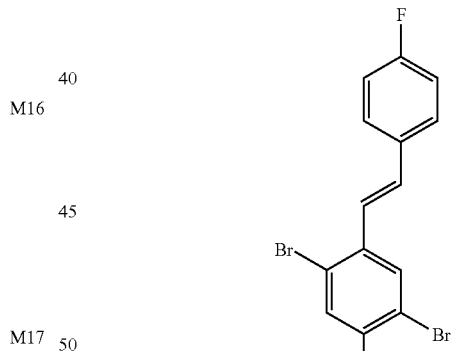
M23
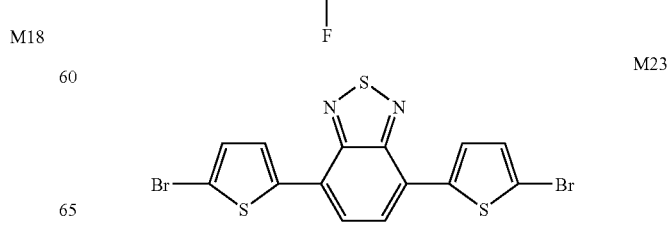

Part B: Preparation of the Polymers

Synthesis of Polymer P1:

Polymer Having an Alternating Hole Conductor Backbone Block Linked to Random Emitter Backbone Sections 0.6069 g (0.8 mmol) of monomer M9, 0.5765 g (0.72 mmol) of monomer M2 and 3.91 g of potassium phosphate hydrate were dissolved in 25 ml of toluene, 25 ml of dioxane and 6.8 ml of water (all solvents oxygen-free). The reaction solution was degassed by means of argon for 30 minutes. 0.45 mg of Pd(OAc)$_2$ and 3.65 mg of P(o-tolyl)$_3$ were then added as catalyst, and the solution was refluxed under an argon atmosphere for 4 hours. A molecular weight of M$_n$=13.7 kDa and M$_w$ 34.4 kDa was determined for the block. 0.8118 g (1.2 mmol) of monomer M7, 0.9248 g (1.2 mmol) of monomer M8, 1.6333 g (2.04 mmol) of monomer M2, 0.9825 g (1.2 mmol) of monomer M1 and 0.8185 g (0.8 mmol) of monomer M19 were subsequently added and the mixture was refluxed for a further 5 hours. End capping was then carried out by adding 0.1 ml of bromobenzene and 50 ml of toluene, the mixture was then refluxed for 1 hour, 200 mg of benzeneboronic acid and 40 ml of toluene were added and the mixture was refluxed for 1 hour. The polymer solution was diluted with 100 ml of toluene and stirred with 100 ml of 0.01% strength aqueous NaCN solution at 60° C. for 3 hours. The phases were then separated and the organic phase was washed with 4×100 ml of H$_2$O. The polymer was precipitated by dropwise introduction into twice the volume of methanol and was filtered off. Further purification was effected by dissolution in 500 ml of THF at 60° C. under argon, filtration through Celite and reprecipitation by addition of twice the volume of methanol. The polymer was filtered off and dried under reduced pressure. 4.66 g (93% of theory) of polymer were isolated; M$_w$=993 kDa, M$_n$=200 kDa, polydispersity=5.0.

Synthesis of Polymer P2:

Polymer Having an Alternating Hole Conductor Backbone Block Linked by Partly Random Emitter Backbone Sections The synthesis was carried out in a manner analogous to P1 using 1.214 g (1.6 mmol) of monomer M9, 1.153 g (1.44 mmol) of monomer M2 and 4.05 g of potassium phosphate hydrate in 25 ml of dioxane, 25 ml of toluene and 7 ml of water for the block and 1.4091 g (1.67 mmol) of monomer M2, 0.5415 g (0.8 mmol) of monomer M7, 0.6165 g (0.8 mmol) of monomer M8, 0.6550 g (0.8 mmol) of monomer M1 and 0.819 g (0.8 mmol) of monomer M19 and 10 ml of dioxane/toluene (1:1) for the random section. Yield: 4.55 g (90% of theory). M$_n$=91 kDa, M$_w$=392 kDa, polydispersity=4.3. Molecular weight of the block: M$_n$=10.2 kDa, M$_w$=27.8 kDa.

Synthesis of Polymer P3:

Polymer Having a Hole Conductor Homoblock Linked by Random Emitter Backbone Sections The synthesis was carried out in a manner analogous to P1 using 0.2021 g (0.44 mmol) of M11 (substituted in the 4 position of the unbrominated phenyl ring by a sec-butyl group), 0.1992 g (0.36 mmol) of monomer BOR1 and 4.05 g of potassium phosphate hydrate in 2.5 ml of dioxane, 2.5 ml of toluene and 20 ml of water for the block and 1.624 g (2.4 mmol) of monomer M7, 0.295 g (0.36 mmol) of monomer M1, 2.914 g (3.64 mmol) of monomer M2 and 0.818 g (0.8 mmol) of monomer M19 in 22.5 ml of dioxane and 22.5 ml of toluene for the random sections. Yield: 4.56 g (92% of theory). M$_n$=96 kDa; M$_w$=361 kDa; polydispersity=3.7.

Synthesis of Polymer P4:

Polymer Having a Hole Conductor Homoblock Linked by Random Emitter Backbone Sections The synthesis was carried out in a manner analogous to P1 using 0.1947 g (0.42 mmol) of monomer M11 (substituted in the 4 position of the unbrominated phenyl ring by a sec-butyl group), 0.20.81 g (0.34 mmol) of monomer BOR1 and 4.05 g of potassium phosphate hydrate in 2.5 ml of dioxane, 2.5 ml of toluene and 20 ml of water for the block and 1.6309 g (1.99 mmol) of monomer M1, 1.6077 g (2.01 mmol) of monomer M2, 0.8064 g (1.19 mmol) of monomer M7, 0.9310 g (1.21 mmol) of monomer M8, 0.4010 g (0.39 mmol) of monomer M19 and 0.4558 g (0.41 mmol) of monomer BOR2 in 22.5 ml of dioxane and 22.5 ml of toluene for the fully random sections. Yield: 4.18 g of polymer (87% of theory). M$_n$=78 kDa; M$_w$=304 kDa; polydispersity=3.9.

Synthesis of Polymer P5:

Polymer Having an Alternating Hole Conductor Backbone Block Linked by Partly Random Emitter Backbone Sections The synthesis was carried out in a manner analogous to P1 using 0.6069 g (0.8 mmol) of monomer M9, 0.6085 g (0.76 mmol) of monomer M2 and 4.05 g of potassium phosphate hydrate in 5 ml of toluene, 5 ml of dioxane and 20 ml of water for the block and 1.1496 g (1.6 mmol) of monomer M21, 2.5749 g (3.21 mmol) of monomer M2 and 1.0825 g (1.6 mmol) of monomer M7 in 15 ml of dioxane and 15 ml of toluene for the partly random sections. Yield: 4.62 g (96% of theory) of polymer isolated. M$_w$=297 kDa, M$_n$=72 kDa, polydispersity=4.1. Molecular weight of the block: M$_n$=30.3 kDa, M$_w$=83.6 kDa.

Synthesis of Polymer P6:

Polymer Having a Hole Conductor Homoblock Linked by Partly Random Emitter Backbone Sections The synthesis was carried out in a manner analogous to P1 using 0.2021 g (0.44 mmol) of M11 (substituted in the 4 position of the unbrominated phenyl ring by a sec-butyl group), 0.1992 g (0.36 mmol) of monomer BOR1 and 4.05 g of potassium phosphate hydrate in 2.5 ml of dioxane, 2.5 ml of toluene and 20 ml of water for the block and 1.082 g (1.6 mmol) of monomer M7, 0.295 g (0.36 mmol) of monomer M1, 2.914 g (3.64 mmol) of monomer M2 and 1.149 g (1.6 mmol) of monomer M21 in 17.5 ml of dioxane and 17.5 ml of toluene for the partly random section. Yield: 4.5 g of polymer (98% of theory). M$_n$=70 kDa; M$_w$=296 kDa; polydispersity=4.2.

Synthesis of Polymer P7:

Polymer Having an Alternating Hole Conductor Backbone Block Linked by Partly Random Emitter Backbone Sections The synthesis was carried out in a manner analogous to P1 using 0.6069 g (0.8 mmol) of monomer M9, 0.6085 g (0.76 mmol) of monomer M2 and 4.05 g of potassium phosphate hydrate in 2.5 ml of toluene, 7.5 ml of dioxane and 20 ml of water for the block and 0.1833 g (0.4 mmol) of monomer M23, 0.8231 g (2.8 mmol) of monomer M12 and 2.5941 g (3.24 mmol) of monomer M2 in 22.5 ml of dioxane and 7.5 ml of toluene for the partly random sections. Yield: 3.40 g (92% of theory); M$_w$=149 kDa, M$_n$=53 kDa, polydispersity=2.8. Molecular weight of the block: M$_n$=30.0 kDa, M$_w$=79.4 kDa.

Further polymers were prepared in a manner analogous to the descriptions for P1 to P7. The chemical properties are summarized in Table 1. Some comparative polymers (denoted by "C" in the table) which do not contain any blocks and have either a partly random or fully random structure were also prepared by analogous methods. These are also shown in the table. All these polymers were examined for use in PLEDs. The way in which PLEDs can be produced has been described comprehensively in WO 04/037887 and the references cited therein.

The most important device properties (color, efficiency, operating voltage and life) are also shown in the table.

It can clearly be seen that the use of alternating hole conductor backbone blocks leads to a significant reduction in the operating voltage, regardless of the amount of these blocks incorporated. Furthermore, it is clear that, for example, the use of hole conductor homoblocks significantly increases the efficiency and the life of the polymers. At the same time, the emission color of the polymers remains substantially unchanged.

TABLE 1

| Polymer (type)[a] | Proportion of monomers in the polymerization [%] | | | | Block | Remaining polymer |
|---|---|---|---|---|---|---|
| | Monom. 1 | Monom. 2 | Monom. 3 | Monom. 4 | Block | |
| P1 (S) | 50% M1/M2 | 30% M7/M8 | 10% M9 | 10% M19 | altern. M2/M9 | random |
| P2 (S) | 50% M1/M2 | 20% M7/M8 | 20% M9 | 10% M19 | altern. M2/M9 | random |
| P3 (S) | 50% M1/M2 | 30% M7 | 10% M11[f]/BOR1 | 10% M19 | homo. M11/BOR1 | random |
| P4 (S) | 50% M1/M2 | 30% M7/M8 | 10% M11[f]/BOR1 | 10% M19/BOR2 | homo. M11/BOR1 | random |
| P5 (S) | 50% M2 | 20% M7 | 10% M9 | 20% M21 | altern. M2/M9 | partly random |
| P6 (S) | 50% M1/M2 | 20% M7 | 10% M11[f]/BOR1 | 20% M21 | homo. M11/BOR1 | random |
| P7 (S) | 50% M2 | 35% M12 | 10% M9 | 5% M23 | altern. M2/M9 | partly random |
| P8 (S) | 50% M2 | 30% M7 | 10% M19 | 10% M9 | altern. M2/M19 | partly random |
| P9 (S) | 50% M2 | 30% M7 | 10% M19 | 10% M9 | altern. M2/M19 + altern. M2/M9 | partly random |
| P9 (S) | 50% M2 | 30% M7 | 10% M19 | 10% M9 | altern. M2/M19/ M2/M9 | partly random |
| C1 (S) | 50% M1/M2 | 30% M7/M8 | 10% M9 | 10% M19 | — | random |
| C2 (S) | 50% M1/M2 | 20% M7/M8 | 20% M9 | 10% M19 | — | random |
| C3 (S) | 50% M2 | 30% M7 | 10% M11[f] | 10% M19 | — | partly random |
| C4 (S) | 50% M1/M2 | 30% M7/M8 | 10% M11[f]/EM1 | 10% M19/EM3 | — | random |
| C5 (S) | 50% M2 | 20% M7 | 10% M9 | 20% M21 | — | partly random |
| C6 (S) | 50% M2 | 20% M7 | 10% M11[f] | 20% M21 | — | partly random |
| C7 (S) | 50% M2 | 35% M12 | 10% M9 | 5% M23 | — | partly random |

| Polymer (type)[a] | GPC[b] | | Electroluminescence[c] | | | |
|---|---|---|---|---|---|---|
| | $M_w$ [kDa] | $M_n$ [kDa] | CIE x/y[d] | Max. Eff. [Cd/A] | U @ 100 Cd/m² [V] | LT[e] [h] |
| P1 (S) | 993 | 200 | 0.18/0.29 | 5.60 | 3.3 | 2200 |
| P2 (S) | 392 | 91 | 0.18/0.27 | 5.09 | 3.1 | 2000 |
| P3 (S) | 361 | 96 | 0.18/0.31 | 6.19 | 3.9 | 2700 |
| P4 (S) | 304 | 78 | 0.19/0.32 | 6.31 | 4.0 | 3100 |
| P5 (S) | 296 | 72 | 0.31/0.58 | 11.43 | 2.8 | >5000 |
| P6 (S) | 296 (484) | 70 (121) | 0.32/0.58 0.35/0.58 | 14.73 | 3.1 | >7500 |
| P7 (S) | 149 | 53 | 0.67/0.33 | 2.25 | 3.1 | >8000 |
| P8 (S) | 374 | 125 | 0.19/0.33 | 4.5 | 3.8 | 2000 |
| P9 (S) | 456 | 107 | 0.18/0.31 | 5.6 | 3.32 | 3600 |
| P9 (S) | 445 | 125 | 0.18/0.30 | 5.4 | 3.23 | 2700 |
| C1 (S) | 666 | 167 | 0.18/0.29 | 4.84 | 3.9 | 1800 |
| C2 (S) | 561 | 148 | 0.18/0.27 | 4.98 | 3.7 | 1500 |
| C3 (S) | 696 | 228 | 0.17/0.26 | 5.45 | 3.8 | 1300 |
| C4 (S) | 509 | 126 | 0.21/0.33 | 5.94 | 3.9 | 1400 |
| C5 (S) | 497 | 140 | 0.29/0.57 | 10.22 | 3.2 | >5000 |

TABLE 1-continued

|       |     |     |           |      |     |       |
|-------|-----|-----|-----------|------|-----|-------|
| C6 (S) | 624 | 159 | 0.31/0.58 | 8.97 | 2.9 | 2500  |
| C7 (S) | 472 | 63  | 0.68/0.32 | 1.92 | 3.5 | >5000 |

[a]S = prepared by Suzuki polymerization (cf. Exp. P1),
[b]GPC measurements in THF; 1 ml/min, PIgel 10 μm Mixed-B 2 × 300 × 7.5 mm$^2$, 35° C., RI detection calibrated against polystyrene
[c]For production of the polymeric LEDs, see part C.
[d]CIE coordinates: chromaticity coordinates of the Commission Internationale de l'Eclairage of 1931.
[e]The life indicated is based on the LT50 value, i.e. the time which elapses until the respective PLED has only 50% of the initial luminance: the values were extrapolated to an initial luminance of 100 Cd/m$^2$.
[f]The monomer M11 is substituted by a sec-butyl group in the para position relative to the nitrogen in the unbrominated phenyl ring.

The invention claimed is:

1. A conjugated copolymer comprising a plurality of block structures which can be the same or different and which has at least one of the following properties:
   a) charge transport block (for hole or electron transport),
   b) charge injection block (for the injection of positive charges or the injection of negative charges),
   c) emitting block,
   d) block which aids the transition from singlet excitons to triplet excitons, or
   e) polymer backbone block,
wherein these block structures are linked by random or partly random polymer sections and wherein the random or partly random polymer sections are made up of at least four different monomers.

2. The polymer as claimed in claim 1, wherein the blocks are homoblocks.

3. The polymer as claimed in claim 1, wherein the blocks are alternating blocks.

4. The polymer as claimed in claim 1, wherein the blocks influence hole injection or hole transport, electron injection or electron transport, the transition from singlet excitons to triplet excitons, emission of light or a plurality of these properties at the same time.

5. The polymer as claimed in claim 1, wherein at least one type of block is hole conductor homoblocks.

6. The polymer as claimed in claim 1, wherein at least one type of block is alternating hole conductor backbone blocks.

7. The polymer as claimed in claim 1, wherein at least one type of block is emitter homoblocks.

8. The polymer as claimed in claim 1, wherein at least one type of block is alternating emitter backbone blocks.

9. The polymer as claimed in claim 1, wherein the proportion of monomers present in blocks is at least 10 mol %.

10. The polymer as claimed in claim 1, wherein the molecular weight Mw of the blocks is in the range from $10^3$ to $3\times10^5$ g/mol.

11. The polymer as claimed in claim 1, wherein the proportion of monomers present in random or partly random sections is at least 10 mol %.

12. The polymer as claimed in claim 1, wherein an average of at least 5 repeating units are present in the partly random polymer sections.

13. The polymer as claimed in claim 1, wherein the polymer comprises structural elements selected from among meta- or para-phenylenes, 1,4-naphthylenes, 9,10-anthracenylenes, 2,7-phenanthrenylenes, 2,7-(9, 10-dihydro)phenanthrenylenes, 1,6- or 2,7- or 4,9-pyrenes and 2,7-tetrahydropyrenes, oxadiazolylenes, 2,5-thiophenylenes, 2,5-pyrrolylenes, 2,5-furanylenes, 2, 5-pyridylenes, 2,5-pyrimidinylenes, 3,6- or 2,7-carbazolylenes, 5, 8-quinolinylenes, fluorenes, spiro-9,9'-bifluorenes and indenofluorenes.

14. The polymer as claimed in claim 13, wherein the polymer comprises structural elements selected from among spiro-9,9'-bifluorenes, fluorenes, 2,7-(9,10-dihydro)phenanthrenylenes and/or indenofluorenes.

15. The polymer as claimed in claim 1, wherein the polymer comprises structural units which influence charge injection or charge transport.

16. The polymer as claimed in claim 15, wherein the structural units are selected from among triarylamines, oxadiazoles, pyridines, pyrimidines, pyrazines and quinolines.

17. The polymer as claimed in claim 1, wherein the polymer comprises structural units which shift the color of the emission.

18. The polymer as claimed in claim 17, wherein the structural elements are selected from among arylene-vinylene or arylene-acetylene structures, e.g. substituted or unsubstituted stilbenyls, tolanyls, bisstyrylarylenes, bis(arylacetylene) arylenes, and larger aromatic units, e.g. chrysenes, naphthacenes, pentacenes, perylenes or coronenes, and heterocyclic units, e.g. thiophene or 2,1,3-benzothiadiazole.

19. The polymer as claimed in claim 1, wherein structural elements which make transfer of single excitons to triplet excitons possible and emit light from the triplet state are present.

20. A blend comprising one or more polymers as claimed in claim 1.

21. A solution comprising one or more polymers as claimed in claim 1 or a blend comprising one or more polymers as claimed in claim 1 in one or more solvents.

22. An electronic device comprising one or more active layers of which at least one comprises one or more polymers as claimed in claim 1 or a blend comprising one or more polymers as claimed in claim 1.

23. The electronic device as claimed in claim 22, wherein said device is a polymeric light-emitting diode (PLED), an organic integrated circuit (O-IC), an organic field effect transistor (OFET), an organic thin film transistor (OTFT), an organic solar cell (O-SC), an organic laser diode (O-laser) or a device for nonlinear optics.

* * * * *